US007749990B2

(12) United States Patent
Hodge et al.

(10) Patent No.: US 7,749,990 B2
(45) Date of Patent: Jul. 6, 2010

(54) COMPOSITIONS FOR THE TREATMENT OF METABOLIC DISORDERS

(75) Inventors: Kirvin L. Hodge, Laurel, MD (US); Shalini Sharma, Gaithersburg, MD (US); Reid W. von Borstel, Potomac, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 0 days.

(21) Appl. No.: 12/208,877

(22) Filed: Sep. 11, 2008

(65) Prior Publication Data

US 2009/0005451 A1 Jan. 1, 2009

Related U.S. Application Data

(62) Division of application No. 10/554,586, filed as application No. PCT/US2004/012141 on Apr. 20, 2004, now Pat. No. 7,442,796.

(60) Provisional application No. 60/466,663, filed on Apr. 30, 2003.

(51) Int. Cl.
A61K 31/66 (2006.01)
A61K 31/435 (2006.01)
A61K 31/38 (2006.01)
A61K 31/235 (2006.01)
A61K 31/12 (2006.01)

(52) U.S. Cl. .................. 514/183; 514/277; 514/430; 514/438; 514/532; 514/685

(58) Field of Classification Search .............. 514/183, 514/277, 430, 438, 532, 685
See application file for complete search history.

(56) References Cited

U.S. PATENT DOCUMENTS

| 4,143,166 | A | 3/1979 | Takaya et al. | |
|---|---|---|---|---|
| 4,474,692 | A | 10/1984 | Oka et al. | |
| 4,474,809 | A | 10/1984 | Floyd, Jr. et al. | |
| 4,956,387 | A | 9/1990 | Wenderoth et al. | |
| 5,028,738 | A | 7/1991 | Hirai et al. | |
| 5,453,443 | A | 9/1995 | Perrier et al. | |
| 5,589,492 | A | 12/1996 | Haigh | |
| 5,665,387 | A | 9/1997 | Mathieu et al. | |
| 6,211,234 | B1 | 4/2001 | Astles et al. | |
| 6,858,602 | B2 * | 2/2005 | Sharma et al. | 514/183 |
| 6,916,848 | B2 | 7/2005 | Sharma | |
| 6,924,314 | B2 * | 8/2005 | Sharma et al. | 514/675 |
| 6,946,491 | B2 | 9/2005 | Sharma et al. | |
| 7,012,071 | B2 | 3/2006 | Sharma et al. | |
| 7,041,659 | B2 | 5/2006 | Sharma | |
| 7,045,541 | B2 | 5/2006 | Sharma | |
| 7,101,910 | B2 | 9/2006 | Sharma | |
| 7,329,782 | B2 | 2/2008 | Sharma et al. | |
| 7,361,686 | B2 | 4/2008 | Hodge et al. | |
| 7,442,796 | B2 * | 10/2008 | Sharma et al. | 546/1 |
| 7,514,555 | B2 * | 4/2009 | Hodge et al. | 546/1 |
| 2005/0090555 | A1 | 4/2005 | Sharma et al. | |
| 2006/0014784 | A1 | 1/2006 | Hodge et al. | |
| 2006/0035970 | A1 | 2/2006 | Sharma et al. | |
| 2006/0247309 | A1 | 11/2006 | Hodge et al. | |
| 2007/0105958 | A1 | 5/2007 | Sharma et al. | |
| 2007/0249696 | A1 | 10/2007 | Sharma et al. | |
| 2007/0249719 | A1 | 10/2007 | Sharma et al. | |
| 2007/0265322 | A1 | 11/2007 | Sharma et al. | |

(Continued)

FOREIGN PATENT DOCUMENTS

DE 949521 9/1956

(Continued)

OTHER PUBLICATIONS

Younis, et al., "The prevention of type 2 diabetes mellitus: recent advances", QJ Med., vol. 97, pp. 451-455, 2004.

(Continued)

Primary Examiner—Kevin Weddington
(74) Attorney, Agent, or Firm—Lewis J. Kreisler

(57) ABSTRACT

Agents useful for the treatment of various metabolic disorders, such as insulin resistance syndrome, diabetes, hyperlipidemia, fatty liver disease, cachexia, obesity, atherosclerosis and arteriosclerosis are disclosed.

Formula I

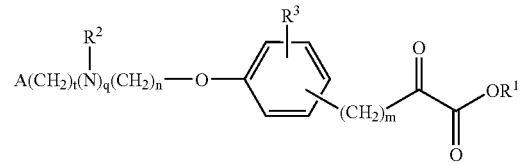

wherein n is 1 or 2; m is 0 to 4; q is 0 or 1; t is 0 or 1; $R^2$ is alkyl having from 1 to 3 carbon atoms; $R^3$ is hydrogen, halo, alkyl having from 1 to 3 carbon atoms, or alkoxy having from 1 to 3 carbon atoms;

A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; and $R^1$ is hydrogen or alkyl having 1 or 2 carbon atoms. Alternatively, when $R^1$ is hydrogen, the biologically active agent can be a pharmaceutically acceptable salt of the compound of Formula I.

8 Claims, No Drawings

U.S. PATENT DOCUMENTS

| | | | |
|---|---|---|---|
| 2007/0282003 | A1 | 12/2007 | Sharma et al. |
| 2008/0015209 | A1 | 1/2008 | Sharma et al. |
| 2008/0015254 | A1 | 1/2008 | Sharma et al. |
| 2008/0021109 | A1 | 1/2008 | Sharma et al. |
| 2008/0027229 | A1 | 1/2008 | Hodge et al. |
| 2008/0306150 | A1 | 12/2008 | Sharma et al. |
| 2008/0306165 | A1 | 12/2008 | Sharma et al. |
| 2008/0319049 | A1 | 12/2008 | Sharma et al. |

FOREIGN PATENT DOCUMENTS

| | | |
|---|---|---|
| EP | 0512352 | 11/1992 |
| JP | 62-61587 | 3/1987 |
| WO | 99/11255 | 3/1999 |
| WO | 01/36365 | 5/2001 |
| WO | 02/100341 | 12/2002 |

OTHER PUBLICATIONS

Goff, et al., "Prevention of Cardiovascular Disease in Persons with type 2 diabetes Mellitus: Current Knowledge and Rational for the Action to Control Cardiovascular Risk in Diabetes (ACCORD) Trial", Am J Cardiol., 99(12A): S4-S20, 2007. (Abstract).

Knowler, et al., "Perspectives in Diabetes: Preventing Non-Insulin-Dependent Diabetes", Diabetes, vol. 44, pp. 483-488, 1995.

Pending (as of Mar. 24, 2008) claims from U.S. Appl. No. 11/772,515.

Pending (as of Mar. 24, 2008) claims from U.S. Appl. No. 11/772,520.

Pending (as of Mar. 24, 2008) claims from U.S. Appl. No. 11/772,560.

Pending (as of Jul. 14, 2008) claims from U.S. Appl. No. 12/160,857.

Pending (as of Jul. 28, 2008) claims from U.S. Appl. No. 12/162,397.

Pending (as of May 7, 2008) claims from U.S. Appl. No. 12/092,932.

Pending (as of Aug. 13, 2008) claims from U.S. Appl. No. 12/279,247.

Pending (as of Aug. 18, 2008) claims from U.S. Appl. No. 12/279,808.

Pending (as of Nov. 10, 2008) claims from U.S. Appl. No. 12/300,239.

Pending (as of Sep. 25, 2008) claims from U.S. Appl. No. 12/294,530.

Pending (as of Dec. 9, 2008) claims from U.S. Appl. No. 12/304,007.

Pending (as of Feb. 13, 2009) claims from U.S. Appl. No. 12/377,460.

Mackay, "American Diabetes Association—62nd Scientific Sessions", IDRUG, 5(7):675-678, 2002.

Youssef, et al., "Diabetes Mellitus Obesity, and Hepatic Steatosis", Seminars in Gastrointestinal Disease, 13(1):17-30, Jan. 2002.

English language translation of JP 62-61587, (1987).

* cited by examiner

COMPOSITIONS FOR THE TREATMENT OF METABOLIC DISORDERS

BACKGROUND OF THE INVENTION

Diabetes mellitus is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction.

There are two primary types of diabetes. Type I, or insulin-dependent diabetes mellitus (IDDM) is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions.

Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance. There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlie many of the major causes of morbidity and death of people over age 40.

Despite the existence of such drugs, diabetes remains a major and growing public health problem. Late stage complications of diabetes consume a large proportion of national health care resources. There is a need for new orally active therapeutic agents which effectively address the primary defects of insulin resistance and islet failure with fewer or milder side effects than existing drugs.

Currently there are no safe and effective treatments for fatty liver disease. Therefore such a treatment would be of value in treating this condition.

WO 02/100341 (Wellstat Therapeutics Corp.) discloses 4-(3-(2,6-Dimethylbenzyloxy)phenyl)-4-oxobutyric acid. WO 02/100341 does not disclose any compounds within the scope of Formula I shown below, in which on the oxo-acid moiety the two oxo groups are immediately adjacent to one another.

SUMMARY OF THE INVENTION

This invention provides a biologically active agent as described below. This invention provides the use of the biologically active agent described below in the manufacture of a medicament for the treatment of insulin resistance syndrome, diabetes, cachexia, hyperlipidemia, fatty liver disease, obesity, atherosclerosis or arteriosclerosis. This invention provides methods of treating a mammalian subject with insulin resistance syndrome, diabetes, cachexia, hyperlipidemia, fatty liver disease, obesity, atherosclerosis or arteriosclerosis comprising administering to the subject an effective amount of the biologically active agent described below. This invention provides a pharmaceutical composition comprising the biologically active agent described below and a pharmaceutically acceptable carrier.

The biologically active agent in accordance with this invention is a compound of Formula I:

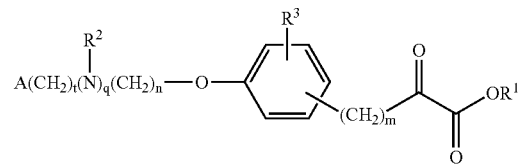

Formula I wherein n is 1 or 2; m is 0, 1, 2, 3 or 4; q is 0 or 1; t is 0 or 1; $R^2$ is alkyl having from 1 to 3 carbon atoms; $R^3$ is hydrogen, halo, alkyl having from 1 to 3 carbon atoms, or alkoxy having from 1 to 3 carbon atoms;

A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; and $R^1$ is hydrogen or alkyl having 1 or 2 carbon atoms. Alternatively, when $R^1$ is hydrogen, the biologically active agent can be a pharmaceutically acceptable salt of the compound of Formula I.

The biologically active agents described above have activity in one or more of the biological activity assays described below, which are established animal models of human diabetes and insulin resistance syndrome. Therefore such agents would be useful in the treatment of diabetes and insulin resistance syndrome. All of the exemplified compounds that were tested demonstrated activity in at least one of the biological activity assays in which they were tested.

DETAILED DESCRIPTION OF THE INVENTION

Definitions

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, bromo, and iodo.

As used herein the term "perfluoro" as in perfluoromethyl or perfluoromethoxy, means that the group in question has fluorine atoms in place of all of the hydrogen atoms.

As used herein "Ac" refers to the group $CH_3C(O)$—.

Certain chemical compounds are referred to herein by their chemical name or by the two-letter code shown below. Compound CQ is included within the scope of Formula I shown above.

BI 4-(3-(2,6-Dimethylbenzyloxy)phenyl)-4-oxobutyric acid

CF 3-(2,6-Dimethylbenzyloxy)phenylacetic acid

CG 3-(2,6-Dimethylbenzyloxy)benzoic acid

CQ [3-(2,6-Dimethylbenzyloxy)-phenyl]-oxoacetic acid

As used herein the transitional term "comprising" is open-ended. A claim utilizing this term can contain elements in addition to those recited in such claim.

Compounds of the Invention

In an embodiment of the agent, use, method or pharmaceutical composition of this invention, n is 1; q is 0; t is 0; $R^3$ is hydrogen; and A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy. In a more specific embodiment, A is 2,6-dimethylphenyl. Examples of such compounds include Compound CQ.

In a preferred embodiment of the biologically active agent of this invention, the agent is in substantially (at least 98%) pure form.

Reaction Schemes

The biologically active agents of the present invention can be made in accordance with the following reaction schemes.

The compound of formula I where m is 0, q is 0, t is 0 or 1, and n is 1 or 2, $R^3$ is hydrogen, halo, alkoxy having from 1 to 3 carbon atoms or alkyl having from 1 to 3 carbon atoms, and $R^1$ is hydrogen or alkyl having from 1 to 2 carbon atoms, $R^2$ is alkyl having from 1 to 3 carbon atoms i.e. compounds of formula:

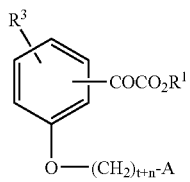

wherein A is described as above, can be prepared via reaction of scheme 1.

In the reaction scheme of Scheme 1, A, t, n, $R^3$ and $R^1$ are as above. Y is a leaving group. The compound of formula II is converted to the compound of formula V via reaction of step (a) using Mitsunobu condensation of II with III using triphenylphosphine and diethyl azodicarboxylate or diisopropyl azodicarboxylate. The reaction is carried out in a suitable solvent for example tetrahydrofuran. Any of the conditions conventionally used in Mitsunobu reactions can be utilized to carry out the reaction of step (a).

The compound of formula V can also be prepared by etherifying or alkylating the compound of formula II with a compound of formula IV via the reaction of step (b) by using suitable base such as potassium carbonate, sodium hydride, triethylamine, pyridine and the like. In the compound of formula IV, Y, include but are not limited to mesyloxy, tosyloxy, chloro, bromo, iodo, and the like. Any conventional conditions to alkylate a hydroxyl group with a leaving group can be utilized to carry out the reaction of step (b). The reaction of step (b) is preferred over step (a) if compound of formula IV is readily available.

The compound of formula V can be converted to the compound of formula VII via reaction of step (c) by oxidation of methyl group with selenium dioxide (VI) in the presence of pyridine. Generally the reaction is carried out at temperatures of from 25° C.-100° C. The product can be isolated and purified by techniques such as extraction, evaporation, chromatography, and recrystallization.

The compound of formula VII is the compound of formula I where m is 0 and $R^1$ is H.

The compound of formula VII can be converted to compound of formula I where $R^1$ is alkyl having from 1 to 2 carbon atoms by esterification using $C_1$-$C_2$ alkyl chloroformate. The reaction can be carried out by using base for example triethylamine and the like. Generally the reaction is carried out in solvent such as ethyl acetate or the like. Generally the reaction is carried out at temperatures of from 0° C. to 25° C. The product can be isolated and purified by techniques such as extraction, evaporation, chromatography, and recrystallization.

Reaction Scheme 1

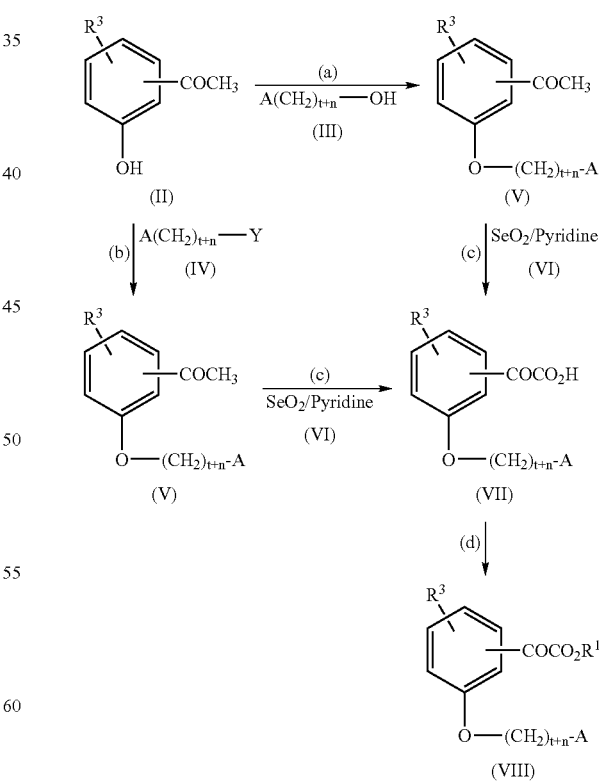

The compound of formula I where m is 0, q is 1, t is 0 or 1, and n is 1 or 2, $R^3$ is hydrogen, halo, alkoxy having from 1 to 3 carbon atoms or alkyl having from 1 to 3 carbon atoms, $R^2$ is alkyl having from 1 to 3 carbon atoms and $R^1$ is hydrogen or alkyl having from 1 to 2 carbon atoms, i.e. compounds of formula:

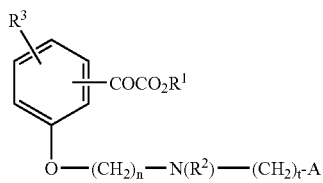

wherein A is described as above, can be prepared via reaction of scheme 2.

In the reaction scheme of Scheme 2, A, t, n, $R^3$ and $R^2$ are as above. Y is chloro or bromo. The compound of formula IX can be mesylated to furnish the compound of formula X via reaction of step (e). Any conventional conditions to carry out the mesylation reaction of a hydroxyl group can be utilized to carry out the step (e). The compound of formula X is then heated with the compound of formula XI to produce the compound of formula XII. Any of the conditions conventional to produce amino alcohol can be utilized to carry out the reaction of step (f).

In the compound of formula XII, alcohol can be displaced by chloro or bromo by treating the compound of formula XII with thionyl chloride, bromine, phosphorus tribromide and the like to produce the compound of formula XIII. Any conventional method to displace alcohol with chloro or bromo can be utilized to carry out the reaction of step (g).

The compound of formula XIII can be reacted with the compound of formula II via reaction of step (h) in the presence of a suitable base such as potassium carbonate, sodium hydride, triethylamine and the like. The reaction is carried out in conventional solvents such as dimethylformamide, tetrahydrofuran and the like to produce the corresponding compound of formula XIV. Any conventional method of etherification of a hydroxyl group in the presence of base (preferred base being potassium carbonate) can be utilized to carry out the reaction of step (h).

The compound of formula XIV can be converted to the compound of formula XV via reaction of step (i) by oxidation of methyl group with selenium dioxide (VI) in the presence of pyridine. Generally the reaction is carried out at temperatures of from 25° C.-100° C. The product can be isolated and purified by techniques such as extraction, evaporation, chromatography, and recrystallization.

The compound of formula XV is the compound of formula I where m is 0 and $R^1$ is H.

The compound of formula XV can be converted to compound of formula I where $R^1$ is alkyl having from 1 to 2 carbon atoms by esterification using $C_1$-$C_2$ alkyl chloroformate. The reaction can be carried out by using base for example triethylamine and the like. Generally the reaction is carried out in solvent such as ethyl acetate or the like. Generally the reaction is carried out at temperatures of from 0° C. to 25° C. The product can be isolated and purified by techniques such as extraction, evaporation, chromatography, and recrystallization.

Reaction Scheme 2

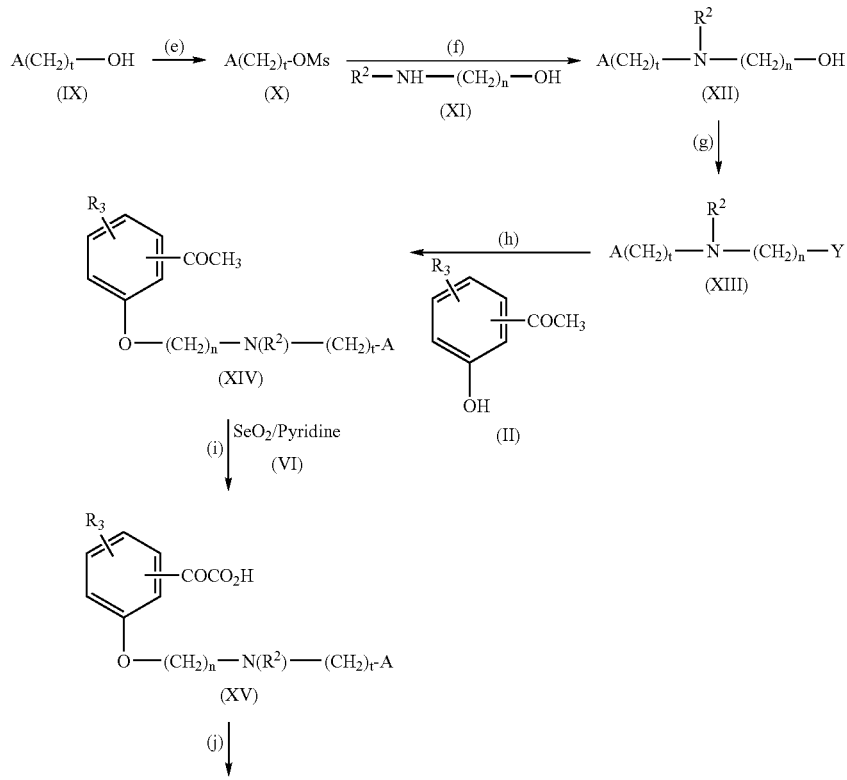

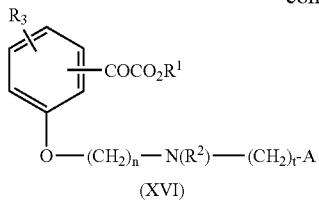

(XVI)

The compound of formula I where m is 1, q is 0 or 1, t is 0 or 1, and n is 1 or 2, $R^3$ is hydrogen, halo, alkoxy having from 1 to 3 carbon atoms or alkyl having from 1 to 3 carbon atoms, and $R^1$ is hydrogen or alkyl having from 1 to 2 carbon atoms, $R^2$ is alkyl having from 1 to 3 carbon atoms i.e. compounds of formula:

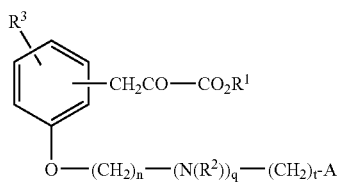

wherein A is described as above, can be prepared via reaction of scheme 3.

In the reaction of Scheme 3, t, n, A, $R^2$, $R^3$ and $R^1$ are as above. Y is chloro or bromo. The compound of formula XVII can be converted to the compound of formula XVIII via reaction of step (k) by reaction with compound of formula III or the compound of formula IV (prepared in the same manner as described in the reaction of scheme 1) or with the compound of formula XIII (prepared in the same manner as described in the reaction of scheme 2). These reactions can be carried out in the same manner as described in connection with reaction steps of (a), (b) or (h).

The compound of formula XVIII can be converted to the compound of formula XIX via reaction of step (1) by reaction with hydantoin in the presence of base for example piperidine. The compound of formula XIX can be converted to the compound of formula XX via reaction of step (m) by treatment with aqueous sodium hydroxide. The compound of formula XX can be converted to the compound of formula XXI via reaction of step (n) by treatment with acid. (Method Adapted from Organic Syntheses; Wiley: New York, 1973; Collect. Vol. 5 p. 627).

The compound of formula XXI is the compound of formula I where m is 1 and $R^1$ is H.

The compound of formula XXI can be converted to compound of formula I where $R^1$ is alkyl having from 1 to 2 carbon atoms by esterification using $C_1$-$C_2$ alkyl chloroformate. The reaction can be carried out by using base for example triethylamine and the like. Generally the reaction is carried out in solvent such as ethyl acetate or the like. Generally the reaction is carried out at temperatures of from 0° C. to 25° C. The product can be isolated and purified by techniques such as extraction, evaporation, chromatography, and recrystallization.

In the other method, the compound of formula XVIII can be reacted with the compound of formula XXII in the presence of acetic anhydride and sodium acetate via reaction of step (o) to give the compound of formula XXIII. The compound of formula XXIII can be hydrolyzed by aqueous acid to give the compound of formula XXIV as described in Synthesis, 1992, 793 and J. Org. Chem. 1956, 21, 1149.

The compound of formula XXIV is the compound of formula I where m is 1 and $R^1$ is H.

The compound of formula XXIV can be converted to compound of formula I where $R^1$ is alkyl having from 1 to 2 carbon atoms by esterification using $C_1$-$C_2$ alkyl chloroformate. The reaction can be carried out by using base for example triethylamine and the like. Generally the reaction is carried out in solvent such as ethyl acetate or the like. Generally the reaction is carried out at temperatures of from 0° C. to 25° C. The product can be isolated and purified by techniques such as extraction, evaporation, chromatography, and recrystallization.

Reaction Scheme 3

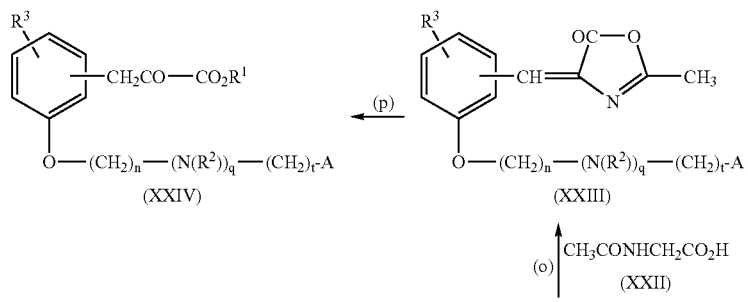

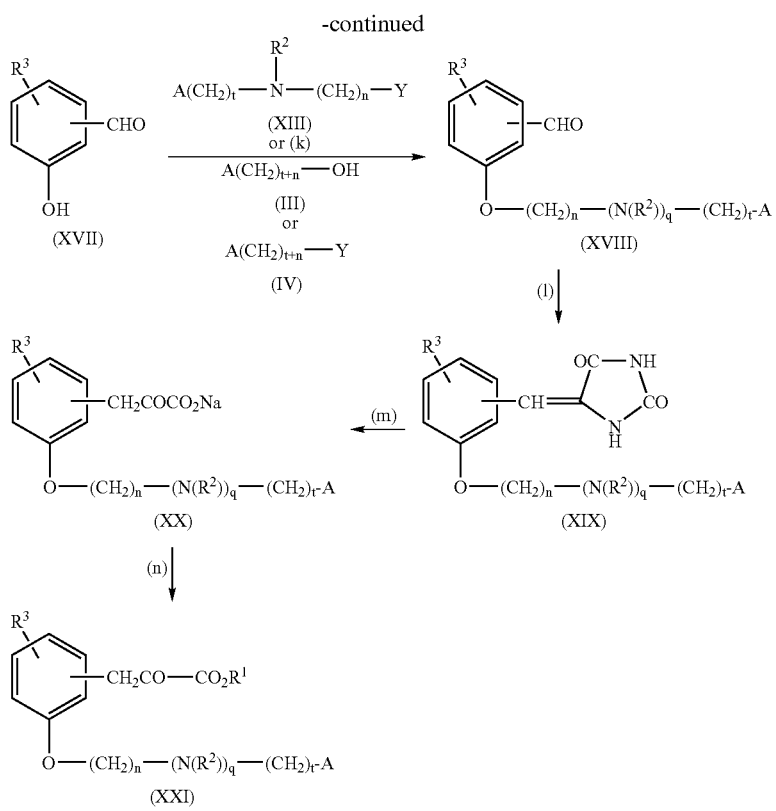

The compound of formula I, where m is 1 and q is 0 or 1, can be synthesized from the compound of formula XXV:

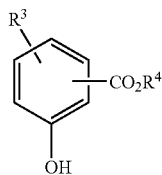

wherein A is described as above, $R^4$ is alkyl group having from 1 to 2 carbon atoms via reaction of scheme 4.

In the reaction of scheme 4, t, n, A, $R^2$, $R^3$, $R^4$ and $R^1$ are as hereinbefore defined. Y is halo. The compound of formula XXV can be converted to the compound of formula XXVI via reaction of step (q) by reaction with compound of formula III or with the compound of formula IV (prepared in the same manner as described in the reaction of scheme 1) or with the compound of formula XIII (prepared in the same manner as described in the reaction of scheme 2). These reactions can be carried out in the same manner as described in connection with reaction steps of (a), (b) or (h).

The compound of formula XXVI can be hydrolyzed via reaction of step (r) to produce acid, which was then subsequently reduced via reaction of step (s) to give alcohol of formula XXVII. The reaction can be carried out by utilizing a conventional reducing agent that converts acid to alcohol. In carrying out this reaction it is generally preferred but not limited to utilize lithium aluminium hydride as the reducing agent. Generally this reaction is carried out in solvents such as tetrahydrofuran. Generally the reaction is carried out at temperatures of from 0° C. to 25° C. The product can be isolated and purified by techniques such as extraction, evaporation, chromatography, and recrystallization.

In the compound of formula XXVII, hydroxyl group can be displaced by chloro or bromo via reaction of step (t). The compound of formula XXVII can be treated with thionyl chloride, bromine, phosphorus tribromide and the like to produce the compound of formula XXVIII.

Any conventional method to displace alcohol with chloro or bromo can be utilized to carry out the reaction of step (t).

The compound of formula XXVIII can be converted to the compound of formula XXIX via reaction of step (u) by carbonylating with CO in organic solvent and base in the presence of metal cluster catalyst for example Co carbonyls (JP 62116541), $[C_6H_5CH_2(CH_3)_3N]^+[FeCo_3(CO)_{12}]^-$(CN 1125217), Co pyridine-2-carboxylate (CN 1279233) and the like.

The compound of formula XXIX is the compound of formula I where m is 1 and $R^1$ is H.

The compound of formula XXIX can be converted to the compound of formula I where $R^1$ is alkyl having from 1 to 2 carbon atoms by esterification using $C_1$-$C_2$ alkyl chloroformate. The reaction can be carried out by using base for example triethylamine and the like. Generally the reaction is carried out in solvent such as ethyl acetate or the like. Generally the reaction is carried out at temperatures of from 0° C. to 25° C. The product can be isolated and purified by techniques such as extraction, evaporation, chromatography, and recrystallization.

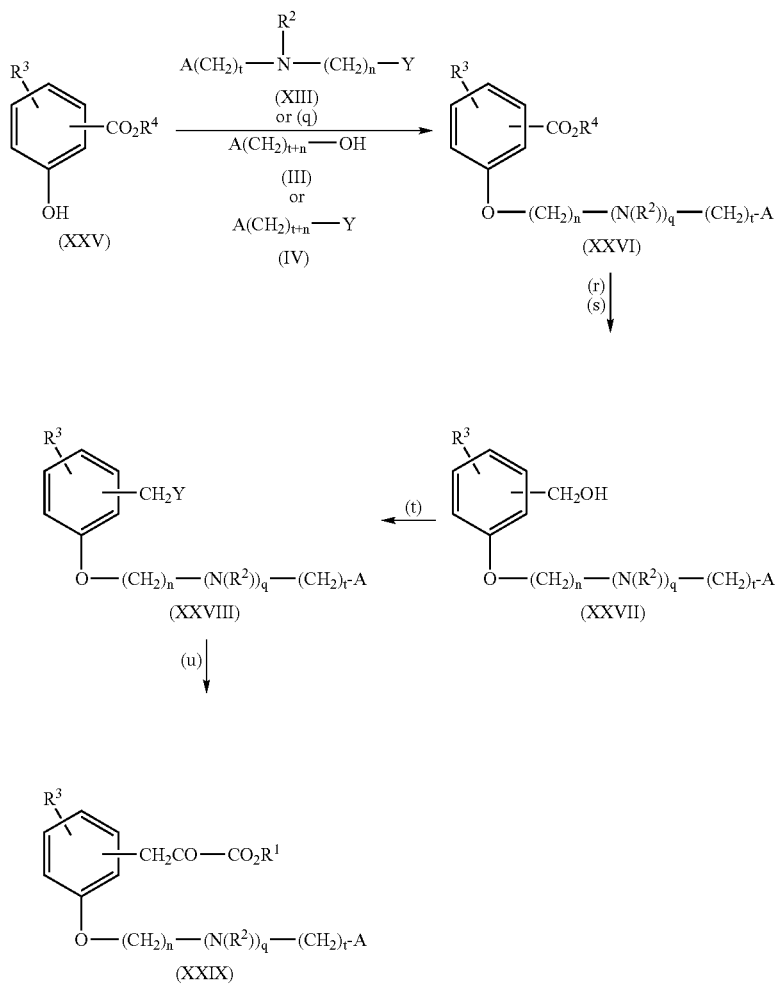

Reaction Scheme 4

The compound of formula I where m is 2, q is 0 or 1, t is 0 or 1, and n is 1 or 2, $R^3$ is hydrogen, halo, alkoxy having from 1 to 3 carbon atoms or alkyl having from 1 to 3 carbon atoms, and $R^1$ is hydrogen or alkyl having from 1 to 2 carbon atoms, $R^2$ is alkyl having from 1 to 3 carbon atoms i.e. compounds of formula:

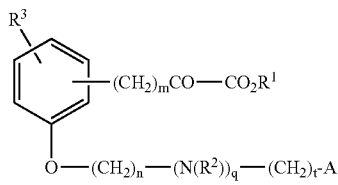

wherein A is described as above, can be prepared via reaction of scheme 5.

In the reaction of scheme 5, t, n, A, $R^2$, $R^3$ and $R^1$ are as hereinbefore defined.

The compound of formula XXXIII can be synthesized by adapting method from EP 387058. The compound of formula XVIII (synthesized in the same manner as described in the connection with reaction of steps (k) in scheme 3) can be reacted with the compound of formula XXX in the presence of base to give the compound of formula XXXI. The compound of formula XXXI can be esterified via reaction of step (w) by treating the acid with a $C_1$-$C_2$ alkyl chloroformate. The reaction can be carried out by using base for example triethylamine and the like. Generally the reaction is carried out in solvent such as ethyl acetate or the like. Generally the reaction is carried out at temperatures of from 0° C. to 25° C. The product can be isolated and purified by techniques such as extraction, evaporation, chromatography, and recrystallization.

The compound of formula XXXII can be reduced by using heterogeneous catalyst such as $PdCl_2/NaBH_4$ in the presence of hydrogen to give compound of formula XXXIII via reaction of step (x).

The compound XXXIII is the compound of formula I where m is 2 and $R^1$ is alkyl having from 1 to 2 carbon atoms. The compound of formula XXXIII can be converted to the compound of formula I where $R^1$ is H by ester hydrolysis.

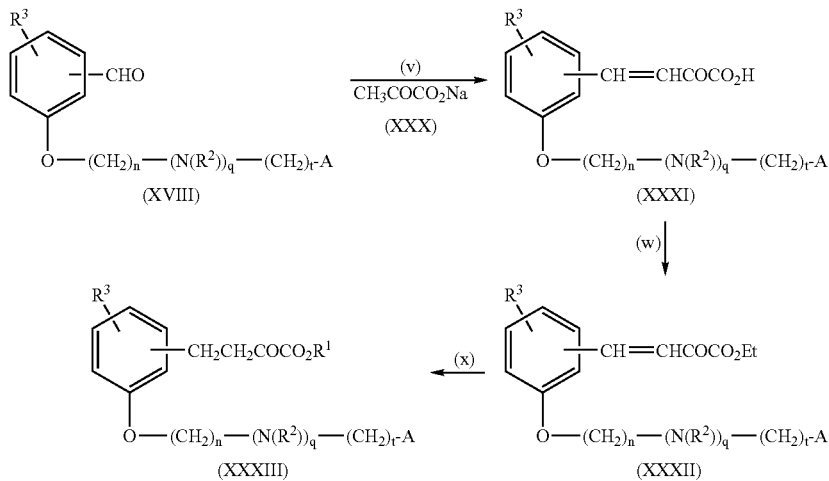

Reaction Scheme 5

The compound of formula I where m is 3 to 4, q is 0 or 1, t is 0 or 1, and n is 1 or 2, $R^3$ is hydrogen, halo, alkoxy having from 1 to 3 carbon atoms or alkyl having from 1 to 3 carbon atoms, and $R^1$ is hydrogen or alkyl having from 1 to 2 carbon atoms, $R^2$ is alkyl having from 1 to 3 carbon atoms i.e. compounds of formula:

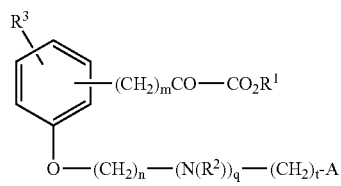

wherein A is described as above, can be prepared via reaction of scheme 6.

In the reaction of scheme 6, t, n, A, $R^2$, and $R^3$ are as hereinbefore defined. $R^1$ is alkyl having from 1 to 2 carbon atoms and p is 3 or 4.

The compound of formula XXXIX can be synthesized by adapting method from J. Org. Chem., Vol. 37, No. 3, 1972, 505-506.

The compound of formula XXXIV can be reacted with the compound of formula XXXV via reaction of step (y) to give compound of formula XXXVI. The reaction can be done using nonaqueous conditions by treatment with boron trifluoroetherate in chloroform. Any of the conditions conventional for these reactions can be utilized to carry out the reaction of step (y).

The compound of formula XXXVI can be alkylated by the compound of formula XXXVII via reaction of step (z) to give the compound of formula XXXVIII. The reaction can be carried out by utilizing a conventional base for example sodium hydride and the like. Generally this reaction is carried out in solvents such as N, N-Dimethylformamide-benzene. The product can be isolated and purified by techniques such as extraction, evaporation, chromatography, and recrystallization.

The compound of formula XXXVIII can be converted to the compound of formula XXXIX via reaction of step (a') by using method as described in Synthesis, 1, 17 (1969).

The compound XXXIX is the compound of formula I where $R^1$ is alkyl having from 1 to 2 carbon atoms. The compound of formula XXXIX can be converted to the compound of formula I where $R^1$ is H by ester hydrolysis.

Reaction Scheme 6

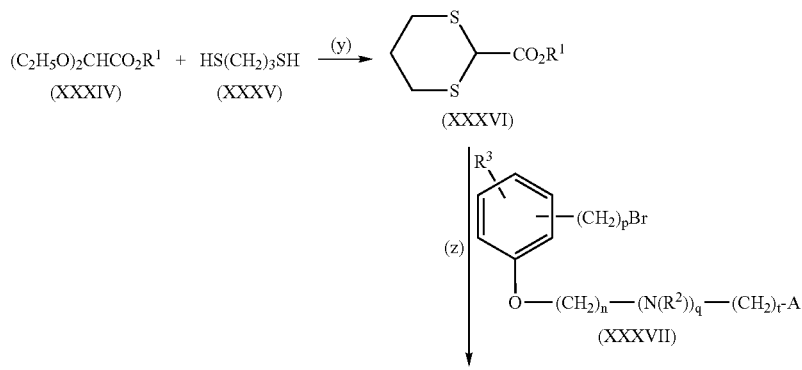

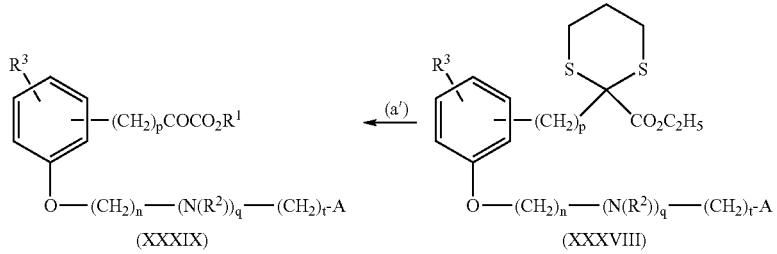

The compound of formula XXXVII where q is 0 or 1, t is 0 or 1, and n is 1 or 2, $R^3$ is hydrogen, halo, alkoxy having from 1 to 3 carbon atoms or alkyl having from 1 to 3 carbon atoms, and $R^2$ is alkyl having from 1 to 3 carbon atoms i.e. compounds of formula:

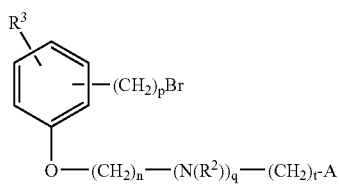

wherein A is described as above, and p is 3 to 4 can be prepared via reaction of scheme 7.

In the reaction of scheme 7, t, n, A, $R^2$, and $R^3$ are as hereinbefore defined. $R^1$ is alkyl having from 1 to 2 carbon atoms and k is 1 to 2. $R^4$ is alkyl group having from 1 to 2 carbon atoms and s is 0 to 1.

The compound of formula XVIII (synthesized in the same manner as described in the reaction scheme 3 via reaction of step (k)) can be converted to the compound of formula XLI via reaction of step (b') using Wittig reaction by treating the compound of formula XVIII with the compound of formula XL. Any conventional method of reacting an aldehyde with triarylphosphine hydrohalide can be utilized to carry out the reaction of step (b'). Any of the conditions conventional in Wittig reactions can be utilized to carry out the reaction of step (b'). The product can be isolated and purified by techniques such as extraction, evaporation, chromatography, and recrystallization.

The compound of formula XLI can be converted to the compound of formula XLII via reaction of step (c') by hydrogenation of double bonds. The reaction can be carried out by using catalyst for example Pd—C, platinum metal or its oxide and the like. Any of the conditions conventional in such hydrogenation reactions can be utilized to carry out the reaction of step (c').

The compound of formula XLII can be converted to the compound of formula XLIII via reaction of step (d') by reducing acid to alcohol. The reaction can be carried out utilizing a conventional reducing agent for example alkali metal hydride such as lithium aluminum hydride. The reaction can be carried out in a suitable solvent, such as tetrahydrofuran. Any of the conditions conventional in such reduction reactions can be utilized to carry out the reaction of step (d').

The compound of formula XLIII can be converted to the compound of formula XXXVII by displacing alcohol with bromo by treating the compound of formula XLIII with bromine, phosphorus tribromide, carbon tetrabromide and the like. Any conventional method to displace alcohol with bromo can be utilized to carry out the reaction of step (e').

Reaction Scheme 7

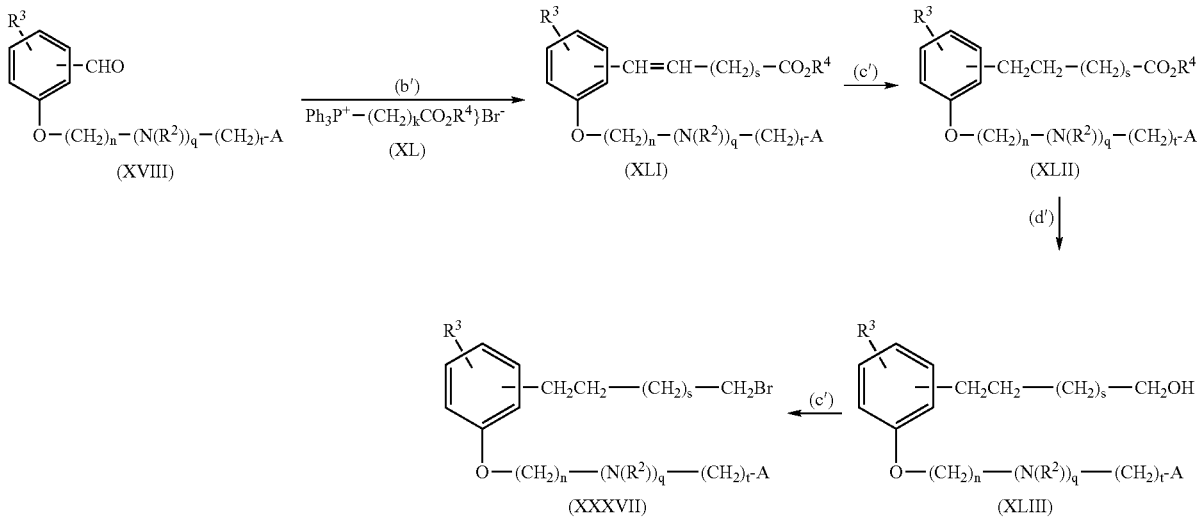

The compound of formula XVII where $R^3$ is hydrogen, halo, alkoxy having from 1 to 3 carbon atoms or alkyl having from 1 to 3 carbon atoms, i.e. compounds of formula:

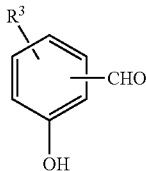

can be prepared via reaction of scheme 8.

In the reaction scheme of Scheme 8, $R^4$ is alkyl group having from 1 to 2 carbon atoms, and P is a protecting group.

The compound of formula XXV can be converted to the compound of formula XLIV via the reaction of step (f') by protecting the hydroxy group and then deprotecting the ester group by utilizing suitable protecting and deprotecting groups such as those described in Protecting Groups in Organic Synthesis by T. Greene.

The compound of formula XLIV can be converted to the compound of formula XLV via reaction of step (g') by reducing acid to alcohol. The reaction can be carried out utilizing a conventional reducing agent for example alkali metal hydride such as lithium aluminum hydride. The reaction can be carried out in a suitable solvent, such as tetrahydrofuran. Any of the conditions conventional in such reduction reactions can be utilized to carry out the reaction of step (g').

The compound of formula XLV can be converted to the compound of formula XLVI via reaction of step (h') by oxidation of alcohol to the aldehyde. The reaction can be carried out utilizing a suitable oxidizing agent for example pyridinium chlorochromate, dimethyl sulfoxide activated by 2,4,6-trichloro[1,3,5]-triazine (cyanuric chloride, TCT) under Swern oxidation conditions (J.O.C. 2001, 66, 7907-7909) and the like. Any of the conditions conventional in such oxidation reactions can be utilized to carry out the reaction of step (h'). In the compound of formula XLVI, the hydroxy group can be deprotected via reaction of step (i') by utilizing suitable deprotecting groups such as those described in Protecting Groups in Organic Synthesis by T. Greene to give the compound of formula XVII.

Reaction Scheme 8

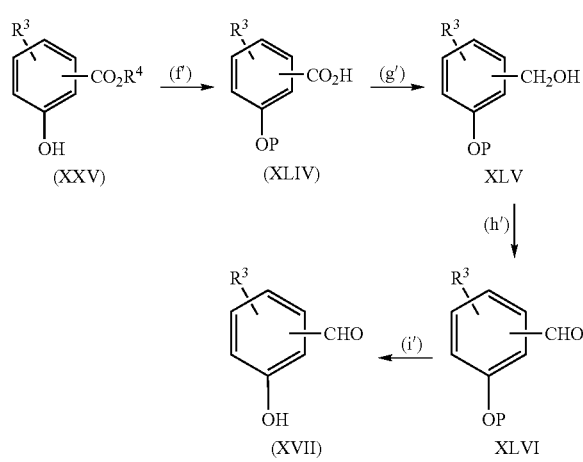

The compound of formula XL, where $R^4$ is alkyl group having from 1 to 2 carbon atoms and k is 1 to 2, i.e. compounds of formula:

$$Ph_3P^+\!-\!(CH_2)_k\!-\!CO_2R^4\}Br^-$$

can be prepared via reaction of scheme 9.

In the reaction scheme of Scheme 9, $R^4$ and k are as above.

The compound of formula XLVII can be reacted with the compound of formula XLVIII via the reaction of step (j') to give compound of formula XL. Any of the conditions conventionally used in reacting triphenylphosphine with hydrohalide can be utilized to carry out the reaction of step (j').

Reaction Scheme 9

$$Ph_3P + Br(CH_2)_kCO_2R^4 \xrightarrow{(j')} Ph_3P^+\!-\!(CH_2)_kCO_2R^4\}Br^-$$
(XLVII)   (XLVIII)                      (XL)

The compound of formula III, $$A(CH_2)_{t+n}\!-\!OH$$

and the compound of formula IV, where t is 0 or 1, n is 1 or 2, i.e. compounds of formula:

$$A(CH_2)_{t+n}\!-\!Y$$

wherein A is described as above, and Y is a leaving group, can be prepared via reaction of scheme 10.

In the reaction of Scheme 10, A is described as above and Y is a leaving group. The compound of formula XLIX can be reduced to the compound of formula L via reaction of step (k'). The reaction is carried out utilizing a conventional reducing agent for example alkali metal hydride such as lithium aluminum hydride. The reaction is carried out in a suitable solvent, such as tetrahydrofuran. Any of the conditions conventional in such reduction reactions can be utilized to carry out the reaction of step (k').

The compound of formula L is the compound of formula III where t is 0 and n is 1.

The compound of formula L can be converted to the compound of formula LI by displacing hydroxyl group with a halogen preferred halogen being bromo or chloro. Appropriate halogenating reagents include but are not limited to thionyl chloride, bromine, phosphorous 24 tribromide, carbon tetrabromide and the like. Any conditions conventional in such halogenation reactions can be utilized to carry out the reaction of step (1'). The compound of formula LI is the compound of formula IV where t is 0 and n is 1.

The compound of formula LI can be converted to the compound of formula LII by reacting LI with an alkali metal cyanide for example sodium or potassium cyanide. The reaction is carried out in a suitable solvent, such as dimethyl sulfoxide. Any of the conditions conventionally used in the preparation of nitrile can be utilized to carry out the reaction of step (m').

The compound of formula LII can be converted to the compound of formula LIII via reaction of step (n') by acid or base hydrolysis. In carrying out this reaction it is generally preferred to utilize basic hydrolysis, for example aqueous sodium hydroxide. Any of the conditions conventionally used in hydrolysis of nitrile can be utilized to carry out the reaction of step (n').

The compound of formula LIII can be reduced to give the compound of formula LIV via reaction of step (o'). This reaction can be carried out in the same manner as described hereinbefore in the reaction of step (k').

The compound of formula LIV is the compound of formula III where t is 1 and n is 1.

The compound of formula LIV can be converted to the compound of formula LV via reaction of step (p') in the same manner as described hereinbefore in connection with the reaction of step (1').

The compound of formula LV is the compound of formula IV where t is 1 and n is 1.

The compound of formula LV can be reacted with diethyl malonate utilizing a suitable base for example sodium hydride to give compound of formula LVI. The reaction is carried out in suitable solvents, such as dimethylformamide, tetrahydrofuran and the like. Any of the conditions conventional in such alkylation reactions can be utilized to carry out the reaction of step (q').

The compound of formula LVI can be hydrolyzed by acid or base to give compound of formula LVII via reaction of step (r').

The compound of formula LVII can be converted to the compound of formula LVIII via reaction of step (s') in the same manner as described hereinbefore in connection with the reaction of step (k').

The compound of formula LVIII is the compound of formula III where t is 1 and n is 2.

The compound of formula LVIII can be converted to the compound of formula LIX via reaction of step (t') in the same manner as described hereinbefore in connection with the reaction of step (1').

The compound of formula LIX is the compound of formula IV where t is 1 and n is 2.

In the reaction of Scheme 11, $R^1$ is H and $R^3$ is halo, alkoxy having from 1 to 3 carbon atoms or alkyl having from 1 to 3 carbon atoms. $R^4$ is alkyl having from 1 to 2 carbon atoms. The compound of formula XXV can be converted to the compound of formula LX via reaction of step (u') by ester hydrolysis.

The compound of formula II can be synthesized from the compound of formula LX via reaction of step (v') by adapting the method of George M Rubottom et al., J. Org. Chem. 1983, 48, 1550-1552.

Reaction Scheme 11

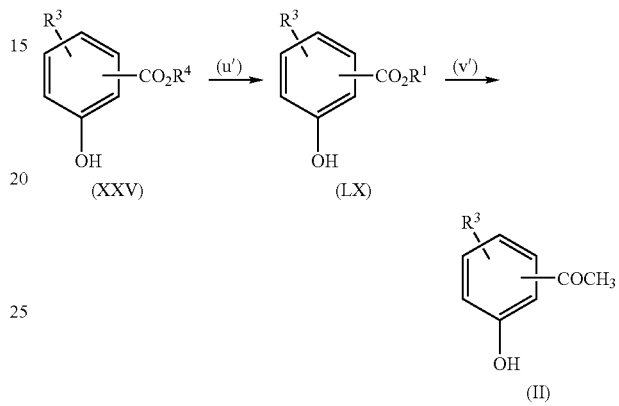

Reaction Scheme 10

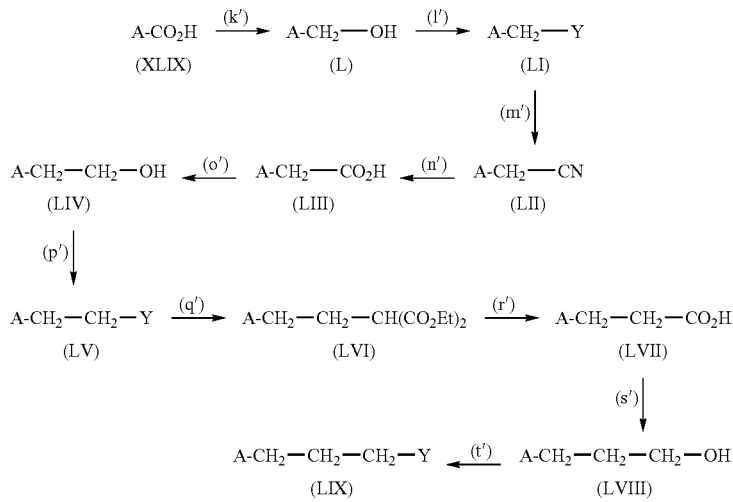

The compound of formula II where $R^3$ is halo, alkoxy having from 1 to 3 carbon atoms or alkyl having from 1 to 3 carbon atoms, i.e. compounds of formula:

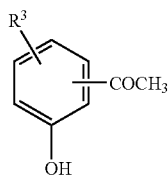

can be prepared via reaction of scheme 11.

The compound of formula LX where $R^1$ is H and $R^3$ is halo, i.e. compounds of formula:

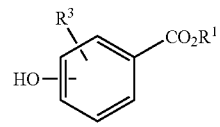

are either commercially available or can be prepared according to the methods described in the literature as follows:
1. 3-Br or F-2-$OHC_6H_3CO_2H$
Canadian Journal of Chemistry (2001), 79(11) 1541-1545.
2. 4-Br-2-$OHC_6H_3CO_2H$
WO 9916747 or JP 04154773.

3. 2-Br-6-OHC$_6$H$_3$CO$_2$H
JP 47039101.
4. 2-Br-3-OHC$_6$H$_3$CO$_2$H
WO 9628423.
5. 4-Br-3-OHC$_6$H$_3$CO$_2$H
WO 2001002388.
6. 3-Br-5-OHC$_6$H$_3$CO$_2$H
Journal of labelled Compounds and Radiopharmaceuticals (1992), 31 (3), 175-82.
7. 2-Br-5-OHC$_6$H$_3$CO$_2$H and 3-Cl-4-OHC$_6$H$_3$CO$_2$H
WO 9405153 and U.S. Pat. No. 5,519,133.
8. 2-Br-4-OHC$_6$H$_3$CO$_2$H and 3-Br-4-OHC$_6$H$_3$CO$_2$H
WO 20022018323
9. 2-Cl-6-OHC$_6$H$_3$CO$_2$H
JP 06293700
10. 2-Cl-3-OHC$_6$H$_3$CO$_2$H
Proceedings of the Indiana Academy of Science (1983), Volume date 1982, 92, 145-51.
11. 3-Cl-5-OHC$_6$H$_3$CO$_2$H
WO 2002000633 and WO 2002044145.
12. 2-Cl-5-OHC$_6$H$_3$CO$_2$H
WO 9745400.
13. 5-I-2-OHC$_6$H$_3$CO$_2$H and 3-I, 2-OHC$_6$H$_3$CO$_2$H
Z. Chem. (1976), 16(8), 319-320.
14. 4-I-2-OHC$_6$H$_3$CO$_2$H
Journal of Chemical Research, Synopses (1994), (11), 405.
15. 6-I-2-OHC$_6$H$_3$CO$_2$H
U.S. Pat. No. 4,932,999.
16. 2-I-3-OHC$_6$H$_3$CO$_2$H and 4-I-3-OHC$_6$H$_3$CO$_2$H
WO 9912928.
17. 5-I-3-OHC$_6$H$_3$CO$_2$H
J. Med. Chem. (1973), 16(6), 684-7.
18. 2-I-4-OHC$_6$H$_3$CO$_2$H
Collection of Czechoslovak Chemical Communications, (1991), 56(2), 459-77.
19. 3-I-4-OHC$_6$H$_3$CO$_2$,
J.O.C. (1990), 55(18), 5287-91.

The compound of formula LX, where $R^1$ is H and $R^3$ is alkoxy having from 1 to 3 carbon atoms, i.e. compounds of formula:

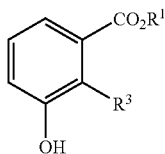

can be synthesized via the reaction of scheme 12.

In the reaction of Scheme 12, $R^1$ and $R^3$ are as above, and $R^4$ is alkyl group having from 1 to 2 carbon atoms.

The compound of formula LXI can be converted to the compound of formula LXII by reducing the aldehyde to primary alcohol. In carrying out this reaction, it is preferred but not limited to use sodium borohydride as the reducing reagent. Any of the conditions suitable in such reduction reactions can be utilized to carry out the reaction of step (w').

The compound of formula LXII can be converted to the compound of formula LXIII via reaction of step (x') by protecting 1-3 Diols by using 1,1,3,3-Tetraisopropyldisiloxane. The suitable conditions for this protecting group can be described in the Protecting Groups in Organic Synthesis by T. Greene.

The compound of formula LXIII can be converted to the compound of formula LXIV via reaction of step (y') by protecting the phenol group using benzyl bromide. The suitable conditions for this protecting group can be described in the Protecting Groups in Organic Synthesis by T. Greene.

The compound of formula LXIV can be converted to the compound of formula LXV by deprotection using tetrabutylammonium fluoride via reaction of step (z'). The suitable conditions for the deprotection can be described in the Protecting Groups in Organic Synthesis by T. Greene.

The compound of formula LXV can be converted to compound of formula LXVI via reaction of step (a") by oxidation. Any conventional oxidizing group that converts primary alcohol to an acid for example chromium oxide and the like can be utilized to carry out the reaction of step (a").

The compound of formula LXVI can be converted to the compound of formula LXVII by esterification of compound of formula LXVI with methanol or ethanol. The reaction can be carried out either by using catalysts for example H$_2$SO$_4$, TsOH and the like or by using dehydrating agents for example dicyclohexylcarbodiimide and the like. Any of the conditions conventional in such esterification reactions can be utilized to carry out the reaction of step (b").

The compound of formula LXVII can be converted to the compound of formula LXVIII by etherifying or alkylating the compound of formula LXVII with methyl halide or ethyl halide or propyl halide by using suitable base for example potassium carbonate, sodium hydride and the like. The reaction is carried out in conventional solvents, such as tetrahydrofuran, dimethylformamide. The reaction is generally carried out at temperatures of from 0° C. to 40° C. Any of the conditions suitable in such alkylation reactions can be utilized to carry out the reaction of step (c").

The compound of formula LXVIII can be converted to the compound of formula LXIX via reaction of step (d") by deprotection of ester and benzyl groups. The suitable deprotecting conditions can be described in the Protecting Groups in Organic Synthesis by T. Greene.

Reaction Scheme 12

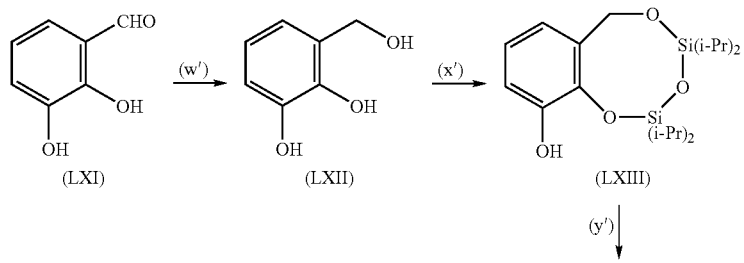

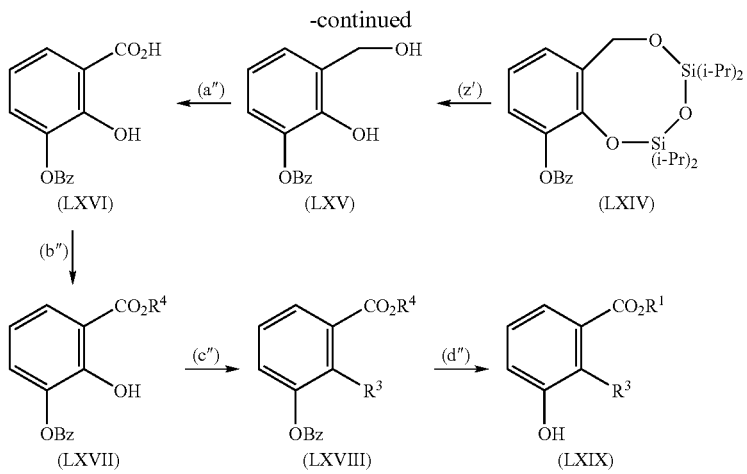

The compound of formula LX, where $R^1$ is H and $R^3$ is alkoxy having from 1 to 3 carbon atoms, i.e. compounds of formula:

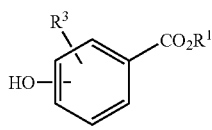

are either commercially available or can be prepared according to the methods described in the literature as follows:
1. 2-OMe-4-OHC$_6$H$_3$CO$_2$H
US 2001034343 or WO 9725992.
2. 5-OMe-3-OHC$_6$H$_3$CO$_2$H
J.O.C (2001), 66(23), 7883-88.
3. 2-OMe-5-OHC$_6$H$_3$CO$_2$H
U.S. Pat. No. 6,194,406 (Page 96) and Journal of the American Chemical Society (1985), 107(8), 2571-3.
4. 3-OEt-5-OHC$_6$H$_3$CO$_2$H
Taiwan Kexue (1996), 49(1), 51-56.
5. 4-OEt-3-OHC$_6$H$_3$CO$_2$H
WO 9626176
6. 2-OEt-4-OHC$_6$H$_3$CO$_2$H
Takeda Kenkyusho Nempo (1965), 24, 221-8.
JP 07070025.
7. 3-OEt-4-OHC$_6$H$_3$CO$_2$H
WO 9626176.
8. 3-OPr-2-OHC$_6$H$_3$CO$_2$H
JP 07206658, DE 2749518.
9. 4-OPr-2-OHC$_6$H$_3$CO$_2$H
Farmacia (Bucharest) (1970), 18(8), 461-6.
JP 08119959.
10. 2-OPr-5-OHC$_6$H$_3$CO$_2$H and 2-OEt-5-OHC$_6$H$_3$CO$_2$H
Adapt synthesis from U.S. Pat. No. 6,194,406 (Page 96) by using propyl iodide and ethyl iodide.
11. 4-OPr-3-OHC$_6$H$_3$CO$_2$H
Adapt synthesis from WO 9626176
12. 2-OPr-4-OHC$_6$H$_3$CO$_2$H
Adapt synthesis from Takeda Kenkyusho Nempo (1965), 24, 221-8 by using propyl halide.
13. 4-OEt-3-OHC$_6$H$_3$CO$_2$H
Biomedical Mass Spectrometry (1985), 12(4), 163-9.
14. 3-OPr-5-OHC$_6$H$_3$CO$_2$H
Adapt synthesis from Taiwan Kexue (1996), 49(1), 51-56 by using propyl halide.

The compound of formula LX, where $R^1$ is H and $R^3$ is an alkyl having from 1 to 3 carbon atoms, i.e. compounds of formula:

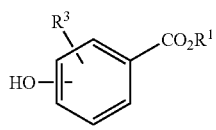

are either commercially available or can be prepared according to the methods described in the literature as follows:
1. 5-Me-3-OHC$_6$H$_3$CO$_2$H and 2-Me-5-OHC$_6$H$_3$CO$_2$H
WO 9619437.
J.O.C. 2001, 66, 7883-88.
2. 2-Me-4-OHC$_6$H$_3$CO$_2$H
WO 8503701.
3. 3-Et-2-OHC$_6$H$_3$CO$_2$H and 5-Et-2-OHC$_6$H$_3$CO$_2$H
J. Med. Chem. (1971), 14(3), 265.
4. 4-Et-2-OHC$_6$H$_3$CO$_2$H
Yaoxue Xuebao (1998), 33(1), 67-71.
5. 2-Et-6-OHC$_6$H$_3$CO$_2$H and 2-n-Pr-6-OHC$_6$H$_3$CO$_2$H
J. Chem. Soc., Perkin Trans 1 (1979), (8), 2069-78.
6. 2-Et-3-OHC$_6$H$_3$CO$_2$H
JP 10087489 and WO 9628423.
7. 4-Et-3-OHC$_6$H$_3$CO$_2$H
J.O.C. 2001, 66, 7883-88.
WO 9504046.
8. 2-Et-5-OHC$_6$H$_3$CO$_2$H
J.A.C.S (1974), 96(7), 2121-9.
9. 2-Et-4-OHC$_6$H$_3$CO$_2$H and 3-Et-4-OHC$_6$H$_3$CO$_2$H
JP 04282345.
10. 3-n-Pr-2-OHC$_6$H$_3$CO$_2$H
J.O.C (1991), 56(14), 4525-29.
11. 4-n-Pr-2-OHC$_6$H$_3$CO$_2$H
EP 279630.
12. 5-n-Pr-2-OHC$_6$H$_3$CO$_2$H
J. Med. Chem (1981), 24(10), 1245-49.
13. 2-n-Pr-3-OHC$_6$H$_3$CO$_2$H
WO 9509843 and WO 9628423.
14. 4-n-Pr-3-OHC$_6$H$_3$CO$_2$H
WO 9504046.
15. 2-n-Pr-5-OHC$_6$H$_3$CO$_2$H
Synthesis can be adapted from J.A.C.S (1974), 96(7), 2121-9 by using ethyl alpha formylvalerate.

16. 3-n-Pr-4-OHC$_6$H$_3$CO$_2$H
Polymer (1991), 32(11) 2096-105.
17. 2-n-Pr-4-OHC$_6$H$_3$CO$_2$H
3-Propylphenol can be methylated to 3-Propylanisole, which was then formylated to 4-Methoxy-3-benzaldehyde. The aldehyde can be oxidized by Jone's reagent to give corresponding acid and deprotection of methyl group by BBr$_3$ will give the title compound.
18. 1. 3-Et-5-OHC$_6$H$_3$CO$_2$H and 3-Pr-n-5-OHC$_6$H$_3$CO$_2$H
Adapt synthesis from J.O.C. 2001, 66, 7883-88 by using 2-Ethylacrolein and 2-Propylacrolein.

Use in Methods of Treatment

This invention provides a method for treating a mammalian subject with a condition selected from the group consisting of insulin resistance syndrome and diabetes (both primary essential diabetes such as Type I Diabetes or Type II Diabetes and secondary nonessential diabetes), comprising administering to the subject an amount of a biologically active agent as described herein effective to treat the condition. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced. This invention also provides a method for treating hyperlipidemia comprising administering to the subject an amount of a biologically active agent as described herein effective to treat the condition. As shown in the Examples, compounds reduce serum triglycerides and free fatty acids in hyperlipidemic animals. This invention also provides a method for treating cachexia comprising administering to the subject an amount of a biologically active agent as described herein effective to treat the cachexia. This invention also provides a method for treating obesity comprising administering to the subject an amount of a biologically active agent as described herein effective to treat the condition. This invention also provides a method for treating a condition selected from atherosclerosis or arteriosclerosis comprising administering to the subject an amount of a biologically active agent as described herein effective to treat the condition. The active agents of this invention are effective to treat hyperlipidemia, fatty liver disease, cachexia, obesity, atherosclerosis or arteriosclerosis whether or not the subject has diabetes or insulin resistance syndrome. The agent can be administered by any conventional route of systemic administration. Preferably the agent is administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitoneal injection), or nasally.

Further embodiments of each of the uses and methods of treatment of this invention comprise administering any one of the embodiments of the biologically active agents described above. In the interest of avoiding unnecessary redundancy, each such agent and group of agents is not being repeated, but they are incorporated into this description of uses and methods of treatment as if they were repeated.

Many of the diseases or disorders that are addressed by the compounds of the invention fall into two broad categories: Insulin resistance syndromes and consequences of chronic hyperglycemia. Dysregulation of fuel metabolism, especially insulin resistance, which can occur in the absence of diabetes (persistent hyperglycemia) per se, is associated with a variety of symptoms, including hyperlipidemia, atherosclerosis, obesity, essential hypertension, fatty liver disease (NASH; non-alcoholic steatohepatitis), and, especially in the context of cancer or systemic inflammatory disease, cachexia. Cachexia can also occur in the context of Type I Diabetes or late-stage Type II Diabetes. By improving tissue fuel metabolism, active agents of the invention are useful for preventing or ameliorating diseases and symptoms associated with insulin resistance, as is demonstrated in animals in the Examples. While a cluster of signs and symptoms associated with insulin resistance may coexist in an individual patient, it many cases only one symptom may dominate, due to individual differences in vulnerability of the many physiological systems affected by insulin resistance. Nonetheless, since insulin resistance is a major contributor to many disease conditions, drugs which address this cellular and molecular defect are useful for prevention or amelioration of virtually any symptom in any organ system that may be due to, or exacerbated by, insulin resistance.

When insulin resistance and concurrent inadequate insulin production by pancreatic islets are sufficiently severe, chronic hyperglycemia occurs, defining the onset of Type II diabetes mellitus (NIDDM). In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because, as is demonstrated in the Examples, active agents and compositions of the invention help to reduce hyperglycemia in diabetes, they are useful for prevention and amelioration of complications of chronic hyperglycemia.

Both human and non-human mammalian subjects can be treated in accordance with the treatment method of this invention. The optimal dose of a particular active agent of the invention for a particular subject can be determined in the clinical setting by a skilled clinician. In the case of oral administration to a human for treatment of disorders related to insulin resistance, diabetes, hyperlipidemia, fatty liver disease, cachexia or obesity the agent is generally administered in a daily dose of from 1 mg to 400 mg, administered once or twice per day. In the case of oral administration to a mouse the agent is generally administered in a daily dose from 1 to 300 mg of the agent per kilogram of body weight. Active agents of the invention are used as monotherapy in diabetes or insulin resistance syndrome, or in combination with one or more other drugs with utility in these types of diseases, e.g. insulin releasing agents, prandial insulin releasers, biguanides, or insulin itself. Such additional drugs are administered in accord with standard clinical practice. In some cases, agents of the invention will improve the efficacy of other classes of drugs, permitting lower (and therefore less toxic) doses of such agents to be administered to patients with satisfactory therapeutic results. Established safe and effective dose ranges in humans for representative compounds are: metformin 500 to 2550 mg/day; glyburide 1.25 to 20 mg/day; GLUCOVANCE (combined formulation of metformin and glyburide) 1.25 to 20 mg/day glyburide and 250 to 2000 mg/day metformin; atorvastatin 10 to 80 mg/day; lovastatin 10 to 80 mg/day; pravastatin 10 to 40 mg/day; and simvastatin 5-80 mg/day; clofibrate 2000 mg/day; gemfibrozil 1200 to 2400 mg/day, rosiglitazone 4 to 8 mg/day; pioglitazone 15 to 45 mg/day; acarbose 75-300 mg/day; repaglinide 0.5 to 16 mg/day.

Type I Diabetes Mellitus: A patient with Type I diabetes manages their disease primarily by self-administration of one to several doses of insulin per day, with frequent monitoring blood glucose to permit appropriate adjustment of the dose and timing of insulin administration. Chronic hyperglycemia leads to complications such as nephropathy, neuropathy, retinopathy, foot ulceration, and early mortality; hypoglycemia due to excessive insulin dosing can cause cognitive dysfunction or unconsciousness. A patient with Type I diabetes is treated with 1 to 400 mg/day of an active agent of this invention, in tablet or capsule form either as a single or a divided dose. The anticipated effect will be a reduction in the dose or frequency of administration of insulin required to maintain blood glucose in a satisfactory range, and a reduced incidence and severity of hypoglycemic episodes. Clinical outcome is monitored by measurement of blood glucose and glycosylated hemoglobin (an index of adequacy of glycemic control integrated over a period of several months), as well as by reduced incidence and severity of typical complications of diabetes. A biologically active agent of this invention can be administered in conjunction with islet transplantation to help maintain the anti-diabetic efficacy of the islet transplant.

Type II Diabetes Mellitus: A typical patient with Type II diabetes (NIDDM) manages their disease by programs of diet and exercise as well as by taking medications such as metformin, glyburide, repaglinide, rosiglitazone, or acarbose, all of which provide some improvement in glycemic control in some patients, but none of which are free of side effects or eventual treatment failure due to disease progression. Islet failure occurs over time in patients with NIDDM, necessitating insulin injections in a large fraction of patients. It is anticipated that daily treatment with an active agent of the invention (with or without additional classes of antidiabetic medication) will improve glycemic control, reduce the rate of islet failure, and reduce the incidence and severity of typical symptoms of diabetes. In addition, active agents of the invention will reduce elevated serum triglycerides and fatty acids, thereby reducing the risk of cardiovascular disease, a major cause of death of diabetic patients. As is the case for all other therapeutic agents for diabetes, dose optimization is done in individual patients according to need, clinical effect, and susceptibility to side effects.

Hyperlipidemia: Elevated triglyceride and free fatty acid levels in blood affect a substantial fraction of the population and are an important risk factor for atherosclerosis and myocardial infarction. Active agents of the invention are useful for reducing circulating triglycerides and free fatty acids in hyperlipidemic patients. Hyperlipidemic patients often also have elevated blood cholesterol levels, which also increase the risk of cardiovascular disease. Cholesterol-lowering drugs such as HMG-CoA reductase inhibitors ("statins") can be administered to hyperlipidemic patients in addition to agents of the invention, optionally incorporated into the same pharmaceutical composition.

Fatty Liver Disease: A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis.

Pharmaceutical Compositions

This invention provides a pharmaceutical composition comprising a biologically active agent as described herein and a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally. The biologically active compounds can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds of the invention. Agents which can advantageously be combined with compounds of the invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds of the invention in single formulations are in accord with the doses used in standard clinical practice. Established safe and effective dose ranges for certain representative compounds are set forth above.

The invention will be better understood by reference to the following examples which illustrate but do not limit the invention described herein.

CHEMICAL SYNTHESIS EXAMPLES

Example 1

(3-(2,6-Dimethylbenzyloxy)-phenyl)-oxoacetic acid

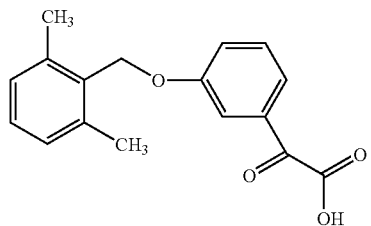

Step A: Preparation of
(3-(2,6-Dimethylbenzyloxy)-phenyl)-oxoacetic acid

To a stirred solution of 1-(3-(2,6-Dimethylbenzyloxy)-phenyl)-ethanone (WO 02/100341, 5 g, 20 mmol) in pyridine (20 ml) was added selenium dioxide (3.492 g, 31 mmol) diluted in pyridine (20 ml). The reaction mixture was heated at 100° C. for 3 hours, decanted from selenium metal and concentrated in vacuo to give orange oil, which solidified at room temperature. The solid was dissolved in saturated NaHCO$_3$ (40 ml) and stirred with decolorizing carbon (0.5 g) for an hour at room temperature. The reaction mixture was filtered through celite and aqueous filtrate was acidified using 6N HCl (6 ml). A gray precipitant (6.3 g) was filtered and dried in vacuo at 40° C. for 2 hours. The acidified filtrate was washed with ether (2×75 ml), dried over Na$_2$SO$_4$, filtered, and concentrated to yield a white solid (0.5 g). Recrystallization using carbon tetrachloride afforded 4.9 g of the title compound with pyridine as an impurity. The semipure material (4.2 g) was dissolved in ethyl acetate (150 ml) and washed with 5% HCl (2×50 ml). The organic layer was dried over Na$_2$SO$_4$, filtered and concentrated to yield a yellow solid (3.9 g). The solid was recrystallized with carbon tetrachloride (30 ml) to afford the title compound (3.03 g) as a light yellow solid.

$^1$H NMR (DMSO): 2.3 (s, 6H); 5.1 (s, 2H); 7.1 (m, 2H); 7.2 (m, 2H); 7.4 (m, 1H); 7.6 (m, 2H).

Biological Activity Examples

For all of the biological activity examples that follow, Compound CQ was produced in accordance with chemical synthesis example 1.

Example 2

Antidiabetic Effects of Compounds of the Invention in Db/db Mice

C57BL/Ksola (db/db) mice have a defect in leptin signaling, leading to hyperphagia, obesity and diabetes. Moreover, unlike ob/ob mice on a C57BL/6J background, db/db mice on a C57BLKS background undergo failure of their insulin-producing pancreatic islet cells, resulting in progression from hyperinsulinemia (associated with peripheral insulin resistance) to hypoinsulinemic diabetes.

Male obese (db/db homozygote) C57BL/Ksola mice approximately 8 weeks of age, were obtained from Jackson Labs (Bar Harbor, Me.) and sorted into groups of 7 animals each animals such that the body weights (40-45 g) and serum glucose levels ($\geq$300 mg/dl in fed state) were similar between groups. A minimum of 7 days was allowed for adaptation after arrival. All animals were maintained under controlled temperature (23° C.), relative humidity (50±5%) and light (7:00-19:00), and allowed free access to standard chow (Formula b Diet 5008, Quality Lab Products, Elkridge, Md.) and water.

Treatment cohorts were given daily oral doses of vehicle (1% hydroxypropylmethylcellulose), Compounds BI, CF, CG, CQ or phenylacetate for 17 days. At the end of the treatment period, blood samples were collected and serum glucose and triglycerides were measured. A statistically significant reduction in blood glucose or triglycerides versus animals treated with oral vehicle is considered a positive screening result for a drug.

TABLE I

The effects of Compounds BI, CF, CG, CQ and phenylacetate in a db/db mouse model of type I diabetes

| Groups | Glucose mg/dL (±SEM) | Triglycerides (mg/dL) |
|---|---|---|
| Vehicle (Control) | 812 ± 34 | 352 ± 27 |
| BI-100 mg/kg | 472 ± 54 | 116 ± 4 |
| BI-150 mg/kg | 348 ± 67 | 90 ± 6 |
| CF-30 mg/kg | 586 ± 31 | 156 ± 20 |
| CF-60 mg/kg | 604 ± 36 | 120 ± 13 |
| CF-100 mg/kg | 391 ± 61 | 92 ± 6 |
| CG-100 mg/kg | 753 ± 24 | 166 ± 14 |
| CQ-60 mg/kg | 691 ± 37 | 175 ± 25 |
| CQ-100 mg/kg | 786 ± 65 | 125 ± 10 |
| Phenylacetate-300 mg/kg | 661 ± 64 | 171 ± 33 |

*p < 0.05 significantly different compared with vehicle-control

What is claimed is:

1. A pharmaceutical composition adapted for oral administration, comprising a pharmaceutically acceptable carrier and from one milligram to four hundred milligrams of a biologically active agent, wherein the agent is a compound of the formula:

Formula I

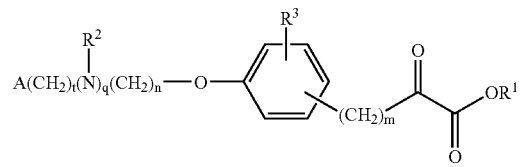

wherein
n is 1 or 2;
m is 0 to 4;
q is 0 or 1;
t is 0 or 1;
R$^2$ is alkyl having from 1 to 3 carbon atoms;
R$^3$ is hydrogen, halo, alkyl having from 1 to 3 carbon atoms, or alkoxy having from 1 to 3 carbon atoms;

A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; and $R^1$ is hydrogen or alkyl having 1 or 2 carbon atoms;

or when $R^1$ is hydrogen, a pharmaceutically acceptable salt of the compound.

2. The pharmaceutical composition of claim 1, wherein n is 1; q is 0; t is 0;

$R^3$ hydrogen; and

A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy.

3. The pharmaceutical composition of claim 2, wherein A is 2,6-dimethylphenyl.

4. The pharmaceutical composition of claim 3, wherein the biologically active agent is [3-(2,6-Dimethylbenzyloxy)-phenyl]-oxoacetic acid.

5. The pharmaceutical composition of claim 4 in oral dosage form.

6. The pharmaceutical composition of claim 3 in oral dosage form.

7. The pharmaceutical composition of claim 2 in oral dosage form.

8. The pharmaceutical composition of claim 1 in oral dosage form.

* * * * *